United States Patent [19]

Denerley

[11] 4,296,032

[45] Oct. 20, 1981

[54] METHOD FOR THE PREPARATION OF PENICILLANIC-β-LACTAMASE INHIBITORS

[75] Inventor: Paul M. Denerley, Horley, England

[73] Assignee: Beecham Group Limited, England

[21] Appl. No.: 135,316

[22] Filed: Mar. 31, 1980

[30] Foreign Application Priority Data

Apr. 4, 1979 [GB] United Kingdom ............... 11764/79

[51] Int. Cl.$^3$ ............................................ C07D 277/60
[52] U.S. Cl. ............................. 260/245.2 R; 424/270
[58] Field of Search ..................... 260/245.2; 424/270

[56] References Cited

U.S. PATENT DOCUMENTS 4,180,506 12/1979 Pratt ................................... 424/270
4,203,992 5/1980 Gordon et al. ............... 260/245.2 R

*Primary Examiner*—Nicholas S. Rizzo
*Attorney, Agent, or Firm*—Jacobs & Jacobs

[57] ABSTRACT

In vivo hydrolyzable esters of 6β-bromopenicillanic acid when substantially free from the corresponding in vivo hydrolyzable ester of 6α-bromopenicillanic acid is useful for their β-lactamase inhibitory activity and may be administered either per se or in combination with a penicillin or cephalosporin.

4 Claims, No Drawings

METHOD FOR THE PREPARATION OF PENICILLANIC-β-LACTAMASE INHIBITORS

This invention relates to penicillanic acid derivatives and in particular to a class of 6 β-bromopenicillanic acid derivatives.

It is known that 6-β-bromopenicillanic acid is a β-lactamase inhibitor [see Loosemore et al., J. Org. Chem., 43, 3611 (1978); Pratt et al., Proc. Natl. Acad. Sci. U.S.A., 75, 4145 (1978); Knott-Hunziker et al., F.E.B.S. Letters, 59, (1979); and Knott-Hunziker et al., Biochem J., 177, 365 (1979)]. However in the past 6-β-bromopenicillanic acid has always been described as a minor component of a mixture together with 6-α-bromopenicillanic acid. No active esters of 6-β-bromopenicillanic acid have yet been described whether pure or in admixture with the corresponding 6-α-compound. The 6-β-bromopenicillanic acid tends to be unstable and is apparently readily isomerised to a mixture with the 6-α-compound. It would be desirable to provide a compound that released 6-β-bromopenicillanic acid in-vivo without producing beforehand dominating quantities of the 6-α-compounds. Such desirable compounds have now been produced.

The present invention provides in-vivo hydrolysable esters of 6-β-bromopenicillanic acid when substantially free from the corresponding in-vivo hydrolysable ester of 6-α-bromopenicillanic acid.

When use of herein the term "substantially free from" means "not contaminated by more than 15% w/w".

More suitably the 6-β-compound of this invention is not contaminated by more than 10% w/w of the corresponding 6-α-compound, favourably is not contaminated by more than 5% w/w of the corresponding 6-α-compound, preferably less than 5% w/w, and preferably is not contaminated by more than 2% w/w w/w of the corresponding 6-α-compound.

The presence of any contaminating 6-α-compound may be estimated by standard analytical techniques such as n.m.r. spectroscopy or h.p.l.c.

In-vivo esters are those which hydrolyse in the human body to produce the parent acid.

The in-vivo hydrolysable nature of the ester may be confirmed by administration to an animal such as a mouse or rat and determination of the presence of 6-bromopenicillanate in the blood or urine of the animal. Alternatively hydrolysis in human blood or serum may be determined.

Suitable in-vivo hydrolysable ester groups are those derivatives of a penicillin (i.e. a 6-β-acylamino penicillanic acid) which are hydrolysable in-vivo.

In-vivo hydrolysable esters of this invention include those of the formula (I):

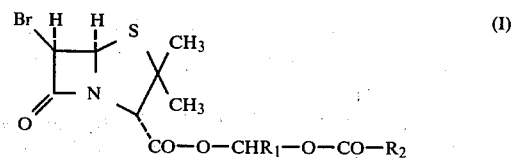

wherein $R_1$ is a hydrogen atom or a methyl group; $R_2$ is an alkyl group of 1 to 6 carbon atoms, a phenyl group, an alkyl group of 1 to 3 carbon atoms substituted by a phenyl group, an alkoxyl group of 1 to 6 carbon atoms, a phenoxyl group, or an alkoxyl group of 1 to 3 carbon atoms substituted by a phenyl group; or $R_1$ is attached to $R_2$ to form a 1,2-diphenylene or 4,5-dimethoxy-1,2-diphenylene group.

Favourably $R_1$ is hydrogen.

When $R_1$ is hydrogen suitably $R_2$ is selected from methyl, ethyl, n-propyl, iso-propyl, n-butyl, tert-butyl, phenyl, benzyl, methoxy, ethoxy, n-propyloxyl and iso-propyloxy. Preferably $R_2$ is tert-butyl.

Favourably $R_1$ and $R_2$ are joined so that the ester is a phthalidyl or 3,4-dimethoxyphthalidyl ester.

Thus preferred in-vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonylethyl, phthalidyl and 5,6-dimethoxyphthalidyl.

Other suitable in-vivo hydrolysable groups include dialkylamino alkyl groups such as dimethylaminomethyl, dimethylaminoethyl, diethylaminomethyl and diethylaminoethyl; and N-phthalimindomethyl and methoxymethyl groups.

The present invention also provides a pharmaceutical composition which comprises an in-vivo hydrolysable ester of 6-β-bromopenicillanic acid and a pharmaceutically acceptable carrier therefor said composition being substantially free from the corresponding in-vivo hydrolysable ester of 6-β-bromopenicillanic acid.

The composition of this invention may be adopted for administration by injection or by the oral route.

Generally the composition will be presented as a unit dose containing from 60 to 600 mgs. of the β-lactamase inhibitor, more suitably 100 to 500 mgs. of the β-lactamase inhibitor and preferably from 125 to 300 mgs. of the inhibitor. Such compositions may be administered 2–6 times daily and usually 3 or 4 times daily in a manner such that the total daily dose for a 70 kg human will be about 200 to 1000 mgs.

The composition of this invention may be administered concurrently or consecutively with a penicillin or cephalosporin. However, it is greatly preferred to administer the penicillin or cephalosporin in the same composition as the β-lactamase inhibitor of this invention. British Patent Specification No. 1,508,978 discloses suitable penicillins and cephalosporins for use in such synergistic compositions. The forms of compositions, methods of preparation and ratios of components disclosed in Specification No. 1,508,978 may be also used with the synergists of this invention. The disclosures of Specification 1,508,978 with respect to compositions are accordingly incorporated herein by reference. A suitable penicillin is amoxycillin as the trihydrate or sodium salt.

The esters of the present invention may be used in such compositions in place of the esters of clavulanic acid.

The present invention also provides a process for the preparation of an in-vivo hydrolysable ester of 6-β-bromopenicillanic acid when substantially free from the corresponding in-vivo hydrolysable ester of 6-α-bromopenicillanic acid which process comprises preparing a mixture of isomeric in-vivo hydrolysable esters of 6α- and 6β-bromopenicillanic acids and thereafter chromatographically separating the mixture of isomers into fractions and recovering the in-vivo hydrolysable ester of 6-β-bromopenicillanic acid from a fraction containing said in-vivo hydrolysable ester of 6-β-bromopenicillanic acid substantially free from the in-vivo hydrolysable ester of a 6-α-bromopenicillanic acid.

The esterification step is generally effected by reaction of the salts with a reactive halide or the like, for example, with a compound of the formula (II):

$$X-CHR_1-O-CO-R_2 \qquad (II)$$

wherein $R_1$ and $R_2$ are as defined in relation to formula (I) and X is Cl, Br or I.

Esterification to afford the dialkylaminoalkyl, N-phthalimidomethyl and methoxymethyl esters is similarly performed, for example using dialkylaminoalkyl halides, N-(chloromethyl)phthalimide and chloromethyl methyl ether respectively.

Alternatively the mixture of isomeric in-vivo hydrolysable esters of 6α- and 6β-bromopenicillanic acid may be prepared by the treatment of an in-vivo hydrolysable ester of 6,6-dibromopenicillanic acid with a strong organic base such as methyl lithium followed by protonation. Protonation is most conveniently effected by acetic acid. The treatment with brine is carried out in anhydrous conditions at a low temperature, for example under nitrogen in a dry solvent at −78° C. In-vivo hydrolysable esters of 6,6-dibromopenicillanic acid are prepared by conventional methods of esterification.

Such esterification reactions to prepare a mixture of isomeric in-vivo hydrolysable esters of 6α- and 6β-bromopenicillanic acids will be carried out under conditions similar to those known to be suitable for the preparation of in-vivo hydrolysable esters of penicillins. For example the reaction may be carried out in an organic solvent such as dimethylformamide, optionally together with methylene chloride.

The salt of the mixture of 6-bromopenicillanic acids may be generated in situ, for example by using an organic tertiary base such as trimethylamine or triethylamine.

Since known mixtures of 6-bromopenicillanic acids contain only a minor proportion (usually about 12% w/w) of the desired 6-β-bromo isomer, the resulting mixture of in-vivo hydrolysable esters only contains a minor proportion of the desired 6-β-bromo isomer. As will be appreciated by the skilled chemist obtaining a reactive minor component from a mixture of materials is difficult and not necessarily possible. Fortunately it has been found that repeated chromatography of the mixture of in-vivo hydrolysable esters can produce the desired in-vivo hydrolysable ester 6-β-bromo isomer substantially free from the corresponding in-vivo hydrolysable ester of the 6-α-bromo isomer.

Suitable methods of chromatography include column chromatography using silica gel as stationary phase. Gradient elution using ethyl acetate/cyclohexane mixtures has been found suitable. The progress of the individual product through the chromatographic system may be monitored by thin layer chromatography and developing with Ehrlich's reagent. The initial major product is the 6-α-isomer and the initial minor product is the 6-β-isomer so that Rf values and relative positions may be known.

Initial separation of the two isomers is not good so that the leading edge of the faster running component or the trailing edge of the slower running component is selected for re-chromatography. Two or three repetitions of this chromatographic process are normally sufficient to produce the desired substantially pure product. In the silica gel ethyl acetate/cyclohexane system described in Example 1 herein the 6-β-isomer is the slower running component so that the trailing edge of the slower running component is selected for re-chromatography.

The 6α, β starting material may be obtained as described in the Loosemore et al., reference referred to hereinbefore.

The following Examples illustrate the process of this invention:

EXAMPLE 1

Preparation of pivaloyloxymethyl 6β-bromopenicillanate (method 1)

6α/β-Bromopenicillanic acid (10 g) was dissolved/suspended in dimethylformamide (600 ml) containing methylene chloride (200 ml) and was treated sequentially with triethylamine (12 ml) and bromomethyl pivalate (10.4 ml) with stirring at 0° C. The reaction was allowed to warm to room temperature and was monitored by thin layer chromatography. After 2 hours, the reaction mixture was evaporated in vacuo to approx. 100 ml; it was diluted with chloroform (400 ml), washed with water (2×400 ml), dried (MgSO$_4$), and evaporated in vacuo to afford a gum. This gum was subjected to column chromatography on silica gel (80 g) using ethyl acetate    iohexane (1:5→1:7). The appropriate fractions were  co.  .oined and evaporated in vacuo to afford pivaloyloxymethyl 6β-bromopenicillanate as an impure gum. This was resubjected to column chromatography on silica gel (80 g) using ethyl acetate:cyclohexane (1:8→1:10) as eluant). The appropriate fractions were combined and evaporated in vacuo to afford pivaloyloxymethyl 6β-bromopenicillanate (0.23 g), i.r. (liq. film) 1790, 1750 cm$^{-1}$, n.m.r. (CDCl$_3$) 1.20 (9H, s, C(CH$_3$)$_3$), 1.48 (3H, s, CH$_3$), 4.52 (1H, s, H-3), 5.32 and 5.56 (2H, 2d, J=4 Hz, H-5 and H-6), 5.8 (2H, ABq J=5 Hz, —CH$_2$—) ppm.

(Combination and evaporation in vacuo of some earlier fractions afforded a mixture of pivaloyloxymethyl 6α-bromopenicillanate and the title compound (1:1) (0.25 g) which could be rechromatographed if desired).

EXAMPLE 2

Preparation of pivaloyloxymethyl 6β-bromopenicillanate (method 2)

Methyllithium (ca 2 M, 4 ml) was added to a solution of pivaloyloxymethyl 6,6-bromopenicillanate (2.75 g) in toluene (150 ml) at −78° under nitrogen. The mixture was stirred at −78° for 10 min. Acetic acid (1 ml) in toluene (10 ml) was then added and the mixture was allowed to come to room temperature. This was washed with water, dried and evaporated to dryness. The residue was chromatographed over silica gel (60 g). Elution of the column with light petrol-ethyl acetate (4:1) gave pivaloyloxymethyl 6β-bromopenicillanate (0.2 g) identical to an authentic sample (t.l.c. and n.m.r. comparisons).

DEMONSTRATION OF EFFECTIVENESS

The MIC of ampicillin was determined in the presence of the pivaloyloxymethyl ester of 6-β-bromopenicillanic acid (inhibitor). The results obtained were as follows:

| Inhibitor conc. (μg/ml) | MIC (μg/ml) of Ampicillin | | | |
|---|---|---|---|---|
| | Staph. aureus Russell | Klebsiella aerogenes E70 | Proteus sp. C889 | E. coli JT. 39 |
| 20 | 0.78 | 6.2 | 8 | 2 |
| 5 | 3.1 | 12.5 | 31 | 4 |

What we claim is:

1. A process for the preparation of an in-vivo hydrolysable ester of 6β-bromopenicillanic acid when substantially free from the corresponding in-vivo hydrolysable ester of 6α-bromopenicillanic acid which process comprises mixing isomeric in-vivo hydrolysable esters of 6α- and 6β-bromopenicillanic acids and thereafter chromatographically separating the mixture of isomers into fractions and recovering the in-vivo hydrolysable ester of 6β-bromopenicillanic acid from a fraction containing said in-vivo hydrolysable ester of 6β-bromopenicillanic acid substantially free from the in-vivo hydrolysable ester of a 6α-bromopenicillanic acid.

2. A process according to claim 1, wherein the mixture of isomeric in vivo hydrolysable esters of 6α- and 6β-penicillanic acids is obtained by dissolving or suspending a mixture of the isomeric acids in a solvent or suspending medium, is treated with triethylamine and then with bromomethyl pivalate to form the pivaloyloxymethyl esters and pivaloyloxymethyl 6β-bromopenicillanate is recovered therefrom substantially free from the 6α-isomer thereof.

3. A process according to claim 1, wherein the mixture of isomeric in vivo hydrolysable esters of 6α- and 6β-penicillanic acids is obtained by dissolving or suspending a mixture of the isomeric acids in a solvent or suspending medium, is treated with triethylamine and then with bromomethyl pivalate to form the pivaloyloxymethyl esters and pivaloyloxymethyl 6β-bromopenicillanate is recovered therefrom substantially free from the 6α-isomer thereof by column chromatography.

4. A process according to claim 1, wherein the mixture of isomeric in vivo hydrolysable esters of 6α- and 6β-penicillanic acids is obtained by dissolving or suspending a mixture of the isomeric acids in a solvent or suspending medium, is treated with triethylamine and then with bromomethyl pivalate to form the pivaloyloxymethyl esters and pivaloyloxymethyl 6β-bromopenicillanate is recovered therefrom substantially free from the 6α-isomer thereof followed by evaporation in vacuo.

* * * * *